United States Patent
Pasquier et al.

(10) Patent No.: US 7,244,278 B2
(45) Date of Patent: Jul. 17, 2007

(54) AGENT AND METHOD FOR OXIDATIVE COLORING OF KERATIN FIBERS

(75) Inventors: Cecile Pasquier, Marly (CH); Veronique Buclin, Morlon (CH); Caroline Kiener, Marly 3 (CH); Nadja Duc-Reichlin, Lully (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 10/579,926

(22) PCT Filed: Nov. 11, 2004

(86) PCT No.: PCT/EP2004/012942

§ 371 (c)(1),
(2), (4) Date: May 19, 2006

(87) PCT Pub. No.: WO2005/060928

PCT Pub. Date: Jul. 7, 2005

(65) Prior Publication Data
US 2007/0067927 A1  Mar. 29, 2007

(30) Foreign Application Priority Data
Dec. 16, 2003 (DE) ................ 103 58 878

(51) Int. Cl.
*A61Q 5/10* (2006.01)
(52) U.S. Cl. ............ 8/406; 8/405; 8/423; 8/426; 8/571; 8/917; 548/161; 548/194; 548/198
(58) Field of Classification Search .......... 8/406, 8/423, 426, 571, 917
See application file for complete search history.

(56) References Cited

U.S. PATENT DOCUMENTS

| 3,634,013 A | 1/1972 | Benshein |
| 7,070,625 B2 * | 7/2006 | Pasquier et al. ........ 8/405 |

FOREIGN PATENT DOCUMENTS

| AT | 282 072 | 6/1970 |
| DE | 1 049 381 | 1/1959 |
| DE | 1 922 400 | 12/1969 |
| DE | 198 56 342 | 6/2000 |
| WO | 02/074268 | 9/2002 |
| WO | WO-2003/042199 | * 5/2003 |

OTHER PUBLICATIONS

Research Disclosure 174, pp. 42-44, Oct. 1978 (in English).

* cited by examiner

Primary Examiner—Fiona T. Powers
(74) Attorney, Agent, or Firm—Michael J. Striker

(57) ABSTRACT

The object of the present invention is a ready-to-use agent for coloring keratin fibers containing (i) at least one heterocyclic hydrazone derivative of formula (I), (ii) at least one aromatic enamine of formula (IIa) or an acid addition compound thereof (IIb) and (iii) at least one oxidant, a multicomponent kit and a method for coloring keratin fibers by use of said agent

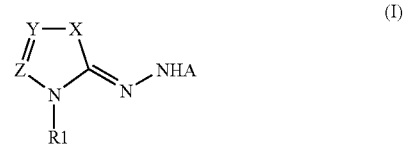

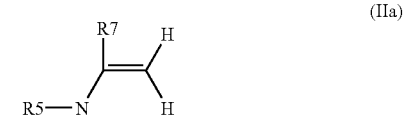

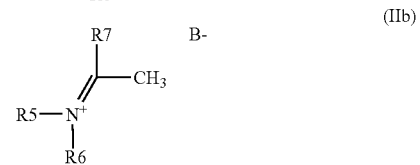

17 Claims, No Drawings

AGENT AND METHOD FOR OXIDATIVE COLORING OF KERATIN FIBERS

CROSS REFERENCE

The invention described and claimed hereinbelow is also described in PCT/EP2004/012942, filed Nov. 15, 2004 in Europe, which, in turn, is based on DE 103 58 878.7, filed Dec. 16, 2003, in Germany. The foregoing patent documents provide the basis for a claim of priority for the invention described and claimed hereinbelow.

BACKGROUND OF THE INVENTION

The object of the present invention is an agent for coloring keratin fibers, for example silk, wool or hair and particularly human hair, said agent containing (i) a heterocyclic hydrazone derivative, (ii) an aromatic enamine and (iii) an oxidant, a multicomponent kit and a method for coloring keratin fibers by use of said coloring agent.

Hair colorants are divided mainly into the groups of oxidation colorants and tinting agents, depending on the initial color of the hair to be dyed and on the desired end result. Oxidation colorants are eminently suited for covering large gray areas, the oxidation colorants used for gray areas of up to 50% as a rule being referred to as oxidative tinting agents, and the oxidation colorants used for gray areas of more than 50% or for "brightening" usually being referred to as oxidative colorants. Direct dyes are contained primarily in non-oxidative colorants (tinting agents). Because of their small molecular size, some direct dyes, for example the nitro dyes, can penetrate into the hair and dye it directly, at least in the outer regions. Such coloring is very gentle to the hair and as a rule can withstand 6 to 8 hair washings. Direct dyes are also frequently used in oxidative colorants for producing certain shades or to intensify the color.

DE-A 1 922 400 discloses the use of hydrazones for coloring keratin fibers. These colorants, however, cannot meet the requirements placed on colorants in every respect, particularly in terms of the luster and intensity of the colorations.

SUMMARY OF THE INVENTION

Surprisingly, we have now found that intense and brilliant colorations can be obtained by use of a combination of certain heterocyclic hydrazones and certain aromatic enamines in the presence of an oxidant.

The object of the present invention is therefore a ready-to-use agent for coloring keratin fibers, such as wool, silk, hair, and particularly human hair, characterized in that it contains (a) at least one hydrazone derivative of formula (I) or a physiologically compatible salt thereof

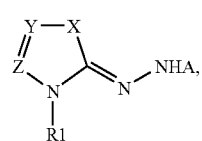
(I)

wherein X denotes oxygen, sulfur or N—R2, Y denotes C—R3 or nitrogen, and Z denotes C—R4 or nitrogen, provided that the heterocyclic part of the compound of formula (I) contains at the most three heteroatoms;

A denotes hydrogen, an acetyl group, a trifluoroacetyl group, a formyl group, a ($C_1$-$C_6$)-alkyl-sulfonyl group or an arylsulfonyl group;

R1 and R2 can be equal or different and independently of each other stand for a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)—($C_1$-$C_{12}$)-alkyl group, a substituted or unsubstituted —C(O)-phenyl group, a —C(O)NH—($C_1$-$C_{12}$)-alkyl group, a substituted or unsubstituted —C(O)NH-phenyl group or a substituted or unsubstituted phenyl group or a benzyl group;

R3 and R4 can be equal or different and independently of each other denote hydrogen, a halogen atom (F, Cl, Br, I), a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a substituted or unsubstituted —C(O)-phenyl group, a substituted or unsubstituted phenyl group, or a naphthyl group; and when Y and Z denote C—R3 and C—R4, R3 and R4 together with the remainder of the molecule can form a heterocyclic or carbocyclic, saturated or unsaturated, substituted or unsubstituted ring system;

(b) at least one aromatic enamine of formula (IIa) or an acid addition salt thereof of formula (IIb)

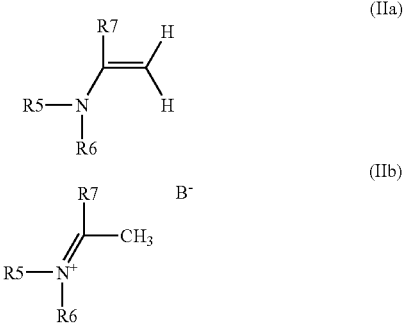

wherein

R5 denotes a mononuclear or polynuclear aromatic group, particularly a 5-membered or 6-membered aryl group (preferably a phenyl group or a naphthyl group) optionally substituted with a ($C_1$-$C_{12}$)-alkyl group, a monohydroxy-($C_1$-$C_{12}$)-alkyl group, a hydroxy group, a ($C_1$-$C_{12}$)-alkoxy group, a di-($C_1$-$C_{12}$)-alkylamino group or a halogen group-substituted 5-membered or 6-membered aryl group (preferably a phenyl group or a naphthyl group) or a 5-membered or 6-membered heterocycle (preferably a pyridyl group);

R6 denotes a ($C_1$-$C_{12}$)-alkyl group, a monohydroxy-($C_1$-$C_{12}$)-alkyl group or a mono-($C_1$-$C_6$)-alkoxy-($C_1$-$C_6$)-alkyl group, wherein oxygen atoms can be present between the carbon atoms of the alkyl chain, and R7 denotes a ($C_1$-$C_{12}$)-alkyl group, a mono-($C_1$-$C_6$)-alkoxy-($C_1$-$C_6$)-alkyl group, a ($C_1$-$C_6$)-alkylene-($C_1$-$C_6$) group, a ($C_1$-$C_6$)-alkoxy-($C_1$-$C_6$)-alkylene group or —O—, NR8- or —S—, wherein
R8 denotes a $(C_1-C_{12})$-alkyl group, a mono-$(C_1-C_6)$-alkoxy-$(C_1-C_6)$-alkyl group, a monohydroxy-$(C_1-C_{12})$-alkyl group or hydrogen, and the R5 and R7 groups together with the nitrogen atom and the carbon atom of the basic enamine structure possibly forming a cyclic linkage, and
B⁻ denotes an anion of an organic or inorganic acid; and
(c) at least one oxidant.

Depending on the pH of the agent, the compound of formula (I) can also exist in equilibrium with the compound of formula (Ia)

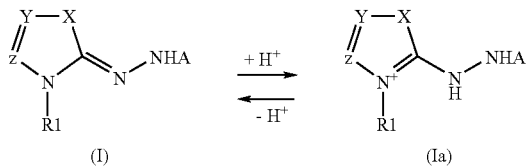

Preferred hydrazones are the hydrazone derivatives of formula (I) or the physiologically compatible salts thereof wherein:
(i) X denotes sulfur, Y denotes C—R3, Z denotes C—R4 and A denotes a hydrogen atom, or
(ii) X denotes N—R2, Y denotes nitrogen and A denotes a hydrogen atom;

the hydrazone derivatives of formula (I) or the physiologically compatible salts thereof wherein X denotes sulfur, Y denotes C—R3, Z denotes C—R4 and A denotes hydrogen being particularly preferred.

The following compounds and the salts thereof are examples of compounds of formula (I):
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
3-methyl-4-(2-naphthalenyl)-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
4,5-diphenyl-3-methyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazole carbonitrile
4,5-dimethyl-3-ethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
3-(1-methylethyl)-4,5-diphenyl-2(3H)-thiazolone hydrazone,
4,5-diphenyl-3-propyl-2(3H)-thiazolone hydrazone,
3-butyl-4,5-diphenyl-2(3H)-thiazolone hydrazone,
4,5-diphenyl-3-(2-methylpropyl)-2(3H)-thiazolone hydrazone,
3-hydroxyethyl-2(3H)-thiazolone hydrazone,
3-hydroxyethyl-4-methyl-2(3H)-thiazolone hydrazone,
3-aminoethyl-2(3H)-thiazolone hydrazone,
3-aminoethyl-4-methyl-2(3H)-thiazolone hydrazone,
3,4-diphenyl-2(3H)-thiazolone hydrazone,
4-methyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
3,4-diphenyl-5-methyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-diphenyl-3-(2-propenyl)-2(3H)-thiazolone hydrazone,
ethyl 2-hydrazono-2,3-dihydro-3-([(phenylamino)carbonyl]-4-methylthiazolecarboxylate
3-methyl-4,5,6,7-tetrahydro-2(3H)-benzothiazolone hydrazone,
3-methyl-2(3H)benzothiazolone hydrazone,
3,6-dimethyl-2(3H)benzothiazolone hydrazone,
6-chloro-3-methyl-2(3H)benzothiazolone hydrazone,
7-chloro-3-methyl-2(3H)benzothiazolone hydrazone,
6-hydroxy-3-methyl-2(3H)benzothiazolone hydrazone,
5-methoxy-3-methyl-2(3H)benzothiazolone hydrazone,
7-methoxy-3-methyl-2(3H)benzothiazolone hydrazone,
5,6-dimethoxy-3-methyl-2(3H)benzothiazolone hydrazone,
5-ethoxy-3-methyl-2(3H)benzothiazolone hydrazone,
6-ethoxy-3-methyl-2(3H)benzothiazolone hydrazone,
3-methyl-5-nitro-2(3H)benzothiazolone hydrazone,
3-methyl-6-nitro-2(3H)benzothiazolone hydrazone,
5-acetamido-3-methyl-2(3H)benzothiazolone hydrazone,
6-acetamido-3-methyl-2(3H)benzothiazolone hydrazone,
5-anilino-3-methyl-2(3H)benzothiazolone hydrazone,
6-anilino-3-methyl-2(3H)benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,

[(2-hydrazono-2,3-dihydro-3-methyl-6-benzothiazolyl)oxy]acetic acid hydrazide,
(3-methyinaphtho[2,3-d]thiazole-2(3H)one hydrazone,
3-ethyl-2(3H)benzothiazolone hydrazone,
6-ethoxy-3-ethyl-2(3H)benzothiazolone hydrazone,
3-propyl-2(3H)benzothiazolone hydrazone,
3-butyl-2(3H)benzothiazolone hydrazone,
3-hexyl-2(3H)benzothiazolone hydrazone,
3-hydroxyethyl-2(3H)benzothiazolone hydrazone,
3-aminoethyl-2(3H)benzothiazolone hydrazone,
3-p-methylbenzyl-2(3H)benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)benzothiazolepropanesulfonic acid,
6-hexadecyloxy-2-hydrazono-3(2H)benzothiazolepropanesulfonic acid,
ethyl 2-keto-3-benzothiazoline acetate hydrazone,
3-acetyl-2(3H)-benzothiazolone hydrazone,
2-hydrazono-3(2H)benzothiazole carboxaldehyde,
3-methyl-2(3H)oxazolone hydrazone,
3-phenyl-2(3H)oxazolone hydrazone,
3-methyl-2(3H)benzoxazolone hydrazone,
3-phenyl-2(3H)benzoxazolone hydrazone,
1,3-dimethyl-4-imidazolin-2-one hydrazone,
1,3-diethyl-4-imidazolin-2-one hydrazone,
1,3-dihydroxyethyl-4-imidazolin-2-one hydrazone,
1,3-diaminoethyl-4-imidazolin-2-one hydrazone,
1,3-dimethyl-4-methoxy-4-imidazolin-2-one hydrazone,
1,3,4-trimethyl-4-imidazolin-2-one hydrazone,
1,3-dimethyl-4-phenyl-4-imidazolin-2-one hydrazone,
4-carboxy-1,3-dimethyl-4-imidazolin-2-one hydrazone,
4-amino-1,3-dimethyl-4-imidazolin-2-one hydrazone,
1,3-dimethyl-4-dimethylamino-4-imidazolin-2-one hydrazone,
1,3-dimethyl-2-benzimidazolinone hydrazone,
1,3-diethyl-2-benzimidazolinone hydrazone,
1,3-dihydroxyethyl-2-benzimidazolinone hydrazone,
1,3-diaminoethyl-2-benzimidazolinone hydrazone,
1,3,5-trimethyl-2-benzimidazolinone hydrazone,
5-methoxy-1,3-dimethyl-2-benzimidazolinone hydrazone,
5-bromo-1,3-dimethyl-2-benzimidazolinone hydrazone,
4,6-dibromo-1,3-dimethyl-2-benzimidazolinone hydrazone,
5-chloro-1,3-dimethyl-2-benzimidazolinone hydrazone,
1,3-dimethyl-5-nitro-2-benzimidazolinone hydrazone,
1,3-dimethyl-6-nitro-2-benzimidazolinone hydrazone,
1,4-dimethyl-Δ2-1,2,4-thiazolone-5-one hydrazone,
1,4-dihydroxyethyl-Δ2-1,2,4-triazoline-5-one hydrazone,
1,4-diaminoethyl-Δ2-1,2,4-triazoline-5-one hydrazone,
1,3,4-trimethyl-Δ2-1,2,4-triazoline-5-one hydrazone,
1,4-dimethyl-3-phenyl-Δ2-1,2,4-trazoline-5-one hydrazone,
1,4-dimethyl-3-methoxy-Δ2-1,2,4-triazoline-5-one hydrazone,
1,4-dimethyl-3-dimethylamino-Δ2-1,2,4-triazoline-5-one hydrazone,
4-carboxy-1,4-dimethyl-Δ2-1,2,4-triazoline-5-one hydrazone,
4-amino-1,4-dimethyl-Δ2-1,2,4-triazoline-5-one hydrazone,
4-butyl-1-methyl-3-phenyl-Δ2-1,3,4-triazoline-5-one hydrazone,
4-methyl-Δ2-1,3,4-thiadiazoline-5-one hydrazone,
4-hydroxyethyl-Δ2-1,3,4-thiadiazoline-5-one hydrazone,
4-aminoethyl-Δ2-1,3,4-thiadiazoline-5-one hydrazone,
4-methyl-2-phenyl-Δ2-1,3,4-thiadiazoline-5-one hydrazone,
2-methoxy-4-methyl-Δ2-1,3,4-thiadiazoline-5-one hydrazone,
2-anilino-4-methyl-Δ2-1,3,4-thiadiazoline-5-one hydrazone,
2-amino-4-methyl-Δ2-1,3,4-thiadiazoline-5-one hydrazone,
2-dimethylamino-4-methyl-Δ2-1,3,4-thiadiazoline-5-one hydrazone,
4-methyl-2-(methylthio)-Δ2-1,3,4-thiadiazoline-5-one hydrazone,
4-(5-hydrazono-4,5-dihydro-4-methyl-1,3,4-thiadiazol-2-yl)benzenesulfonyl fluoride,
4-methyl-Δ2-1,2,4-thiadiazoline-5-one hydrazone,
4-hydroxyethyl-Δ2-1,2,4-thiadiazoline-5-one hydrazone,
4-aminoethyl-Δ2-1,2,4-thiadiazoline-5-one hydrazone,
4-methyl-3-phenyl-Δ2-1,2,4-thiadiazoline-5-one hydrazone,
3-methoxy-4-methyl-Δ2-1,2,4-thiadiazoline-5-one hydrazone,
3-amino-4-methyl-Δ2-1,2,4-thiadiazoline-5-one hydrazone,
3-dimethylamino-4-methyl-Δ2-1,2,4-thiadiazoline-5-one hydrazone,
3-carboxy-4-methyl-Δ2-1,2,4-thiadiazoline-5-one hydrazone,
1,4-dimethyl-Δ2-1,2,4-triazoline-5-one hydrazone,
1,4-dihydroxyethyl-Δ2-1,2,4-triazoline-5-one hydrazone,
1,4-diaminoethyl-Δ2-1,2,4-triazoline-5-one hydrazone,
1,3,4-trimethyl-Δ2-1,2,4-triazoline-5-one hydrazone,
1,4-dimethyl-3-phenyl-Δ2-1,2,4-triazoline-5-one hydrazone and
4-methyl-3-phenyl-Δ2-1,2,4-triazoline-5-one hydrazone.

Among the compounds of formula (I), the following thiazolone hydrazone derivatives and the salts thereof are particularly preferred:
3-methyl-2(3H)thiazolone hydrazone,
3,4-dimethyl-2(3H)thiazolone hydrazone,
4-tert.butyl-3-methyl-2(3H)thiazolone hydrazone,
3-methyl-4-phenyl-2(3H)thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)thiazolone hydrazone,
4-[(1,1'-biphenyl)-4-yl]-3-methyl-2(3H)-thiazolone hydrazone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
4,5-diphenyl-3-methyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-tolyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazino-2,3-dihydro-3-methyl-5-thiazole carbonitrile
4,5-dimethyl-3-ethyl-2(3H)-thiazolone hydrazone,
ethyl 2-hydrazono-2,3-dihydro-3-ethyl-4-methylthiazolecarboxylate, 5-methyl-3-(1-methylethyl)-4-phenyl-2(3H)-thiazolone hydrazone,
4,5-diphenyl-3-(1-methylethyl)-2(3H)-thiazolone hydrazone
4,5-diphenyl-3-propyl-2(3H)-thiazolone hydrazone,
3-butyl-4,5-diphenyl-2(3H)-thiazolone hydrazone,
4,5-diphenyl-3-(2-methylpropyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-diphenyl-3-(2-propenyl)-2(3H)-thiazolone hydrazone,
3-hydroxyethyl-2(3H)-thiazolone hydrazone,
3-hydroxyethyl-4-methyl-2(3H)-thiazolone hydrazone,
3-aminoethyl-2(3H)-thiazolone hydrazone,
3-aminoethyl-4-methyl-2(3H)-thiazolone hydrazone,
3-phenyl-2(3H)-thiazolone hydrazone,
4-methyl-3-phenyl-2(3H)-thiazolone hydrazone,
3,4-diphenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
3,4-diphenyl-5-methyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
ethyl 2-hydrazono-2,3-dihydro-3-[(phenylamino)carbonyl]-4-methylthiazolecarboxylate
3-methyl-4,5,6,7-tetrahydro-2(3H)-thiazolone hydrazone,
3-methyl-2(3H)benzothiazolone hydrazone,
3,6-dimethyl-2(3H)benzothiazolone hydrazone,
6-chloro-3-methyl-2(3H)benzothiazolone hydrazone,
7-chloro-3-methyl-2(3H)benzothiazolone hydrazone,
6-hydroxy-3-methyl-2(3H)benzothiazolone hydrazone,
5-methoxy-3-methyl-2(3H)benzothiazolone hydrazone,
7-methoxy-3-methyl-2(3H)benzothiazolone hydrazone,
5,6-dimethoxy-3-methyl-2(3H)benzothiazolone hydrazone,
5-ethoxy-3-methyl-2(3H)benzothiazolone hydrazone,
6-ethoxy-3-methyl-2(3H)benzothiazolone hydrazone,
3-methyl-5-nitro-2(3H)benzothiazolone hydrazone,
3-methyl-6-nitro-2(3H)benzothiazolone hydrazone,
5-acetamido-3-methyl-2(3H)benzothiazolone hydrazone,
6-acetamido-3-methyl-2(3H)benzothiazolone hydrazone,
5-anilino-3-methyl-2(3H)benzothiazolone hydrazone,
6-anilino-3-methyl-2(3H)benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy] acetic acid hydrazide,
3-methyinaphtho[2,3-d]thiazol-2(3H)one hydrazone
3-ethyl-2(3H)benzothiazolone hydrazone,
6-ethoxy-3-ethyl-2(3H)benzothiazolone hydrazone,
3-propyl-2(3H)benzothiazolone hydrazone,
3-butyl-2(3H)benzothiazolone hydrazone,
3-hexyl-2(3H)benzothiazolone hydrazone,
3-hydroxyethyl-2(3H)benzothiazolone hydrazone,
3-aminoethyl-2(3H)benzothiazolone hydrazone,
3-p-methylbenzyl-2(3H)benzothiazolone hydrazone,
2,3-dihydro-2-hydrazono-3-(2-hydroxyethyl)-6-benzothiazolecarboxylic acid
2,3-dihydro-2-hydrazono-6-methoxy-3(2H)benzothiazolepropanesulfonic acid,
6-hexadecyloxy-2-hydrazono-3(2H)benzothiazolepropanesulfonic acid,
ethyl 2-keto-3-benzothiazolineacetic acid hydrazone,
3-acetyl-2(3H)benzothiazolone hydrazone and
2-hydrazono-3(2H)benzothiazole carboxaldehyde.

Some compounds of formula (I) are commercially available, but they can also be prepared by methods of synthesis known from the literature, for example by the method described in Research Disclosure 174, pp. 42-44 (1978) or in analogy with the method described in DE 1 049 381.

Preferred aromatic enamines are aromatic enamines of formula (IIa) or the physiologically compatible acid addition salts thereof of formula (IIb) wherein the R5 and R7 group together with the nitrogen atom and the carbon atom of the basic enamine structure form a cyclic linkage (particularly a 5-membered or 6-membered ring) wherein R7 is preferably linked to the aromatic group R5 at the carbon atom in the ortho-position to the enamine-substituted carbon.

Particularly suitable acid addition salts of formula (IIb) are those wherein B$^-$ denotes chloride, bromide, iodide, sulfate, hydrogen sulfate, toluenesulfonate, benzenesulfonate, monomethyl sulfate, hexafluorophosphate, hexafluoroantimonate, tetrafluoroborate, tetraphenyl borate, formate, acetate or propionate, with the chloride ion, tetrafluoroborate ion, acetate ion and hydrogen sulfate ion being particularly preferred.

Particularly well suited aromatic enamines of formula (IIa) or the acid addition salts thereof of formula (IIb) are the following compounds
1,3,3-trimethyl-2-methyleneindoline and the salts thereof,
1,3-dimethyl-3-ethyl-2-methyleneindoline and the salts thereof,
3,3-dimethyl-1-(2-hydroxyethyl)-2-methyleneindoline and the salts thereof,
1,3,3,4-tetramethyl-2-methyleneindoline and the salts thereof,
1,3,3,5-tetramethyl-2-methyleneindoline and the salts thereof,
1,3,3,6-tetramethyl-2-methyleneindoline and the salts thereof,
1,3,3,7-tetramethyl-2-methyleneindoline and the salts thereof,
1,3,3,6,7-pentamethyl-2-methyleneindoline and the salts thereof,
1,3,3,5,7-pentamethyl-2-methyleneindoline and the salts thereof,
1,3,3,4,7-pentamethyl-2-methyleneindoline and the salts thereof,
5-chloro-1,3,3-trimethyl-2-methyleneindoline and the salts thereof,
5-fluoro-1,3,3-trimethyl-2-methyleneindoline and the salts thereof,
5-isopropyl-1,3,3-trimethyl-2-methyleneindoline and the salts thereof,
5-hydroxy-1,3,3-trimethyl-2-methyleneindoline and the salts thereof,
5-methoxy-1,3,3-trimethyl-2-methyleneindoline and the salts thereof,
3,3-dimethyl-1-ethyl-5-methoxy-2-methyleneindoline and the salts thereof, 5-nitro-1,3,3-trimethyl-2-methyleneindoline and the salts thereof,
5-amino-1,3,3-trimethyl-2-methyleneindoline and the salts thereof,
5-N-acetylamino-1,3,3-trimethyl-2-methyleneindoline and the salts thereof,
6-hydroxy-1,3,3-trimethyl-2-methyleneindoline and the salts thereof,
6-methoxy-1,3,3-trimethyl-2-methyleneindoline and the salts thereof,
5-methoxy-6-nitro-1,3,3-trimethyl-2-methyleneindoline and the salts thereof,
5-methoxy-6-amino-1,3,3-trimethyl-2-methyleneindoline and the salts thereof,
5-methoxy-6-N-acetylamino-1,3,3-trimethyl-2-methyleneindoline and the salts thereof,
5,6-dihydroxy-1,3,3-trimethyl-2-methyleneindoline and the salts thereof,
5,6-dimethoxy-1,3,3-trimethyl-2-methyleneindoline and the salts thereof,
5,6-methylenedioxy-1,3,3-trimethyl-2-methyleneindoline and the salts thereof,
4,5-dihydroxy-1,3,3-trimethyl-2-methyleneindoline and the salts thereof,
5,7-dihydroxy-1,3,3-trimethyl-2-methyleneindoline and the salts thereof,
5-amino-6-methoxy-1,3,3-trimethyl-2-methyleneindoline and the salts thereof,
5-amino-7-hydroxy-1,3,3-trimethyl-2-methyleneindoline and the salts thereof,
7-amino-5-hydroxy-1,3,3-trimethyl-2-methyleneindoline and the salts thereof,
7-N-acetylamino-5-hydroxy-1,3,3-trimethyl-2-methyleneindoline and the salts thereof,
1,1,2,3-tetramethyl-1H-benz[e]indolinium salts, 2,3-dimethylbenzothiazolium salts and 3-ethyl-2-methylbenzothiazolium salts among which the following compounds are particularly preferred:
1,2,3,3-tetramethyl-3H-indolium chloride,
1,2,3,3-tetramethyl-3H-indolium bromide,
1,2,3,3-tetramethyl-3H-indolium sulfate,
1,2,3,3-tetramethyl-3H-indolium tetrafluoroborate,
3-ethyl-1,2,3-trimethyl-3H-indolium chloride,
3-ethyl-1,2,3-trimethyl-3H-indolium bromide,
3-ethyl-1,2,3-trimethyl-3H-indolium sulfate,
3-ethyl-1,2,3-trimethyl-3H-indolium tetrafluoroborate,
1-ethyl-5-methoxy-2,3,3-trimethyl-3H-indolium chloride,
1-ethyl-5-methoxy-2,3,3-trimethyl-3H-indolium bromide,
1-ethyl-5-methoxy-2,3,3-trimethyl-3H-indolium sulfate,
1-ethyl-5-methoxy-2,3,3-trimethyl-3H-indolium tetrafluoroborate,
5-methoxy-1,2,3,3-tetramethyl-3H-indolium chloride,
5-methoxy-1,2,3,3-tetramethyl-3H-indolium bromide,
5-methoxy-1,2,3,3-tetramethyl-3H-indolium sulfate,
5-methoxy-1,2,3,3-tetramethyl-3H-indolium tetrafluoroborate,
5-nitro-1,2,3,3-tetramethyl-3H-indolium chloride,
5-nitro-1,2,3,3-tetramethyl-3H-indolium bromide,
5-nitro-1,2,3,3-tetramethyl-3H-indolium sulfate and
5-nitro-1,2,3,3-tetramethyl-3H-indolium tetrafluoroborate,
2,3-dimethylbenzothiazolium chloride,
2,3-dimethylbenzothiazolium bromide,
2,3-dimethylbenzothiazolium iodide,
2,3-dimethylbenzothiazolium methylsulfate,
3-ethyl-2-methylbenzothiazolium chloride,
3-ethyl-2-methylbenzothiazolium bromide,
3-ethyl-2-methylbenzothiazolium iodide,
3-ethyl-2-methylbenzothiazolium methylsulfate,
3-ethyl-2-methylbenzothiazolium p-toluenesulfonate.

The colorants of the invention are used in conjunction with an oxidant. Suitable oxidants are those usually employed in hair colorants, for example hydrogen peroxide or the addition compounds thereof, persalts such as the persulfate salts and perborate salts, or peracids and enzymatic oxidation systems, air oxidation also being feasible. Preferred oxidants are hydrogen peroxide or the addition compounds thereof (for example sodium percarbonate, urea peroxide etc) and the persalts such as the persulfate salts or perborate salts, for example potassium persulfate, sodium persulfate or ammonium persulfate as well as mixtures thereof.

The oxidants are contained in the ready-to-use colorant (A) in a total amount from about 0.01 to 10 weight percent and preferably from about 0.1 to 5 weight percent.

Moreover, besides the compounds of formula (I) and compounds of formula (IIa) or (IIb), the colorant of the invention can also contain other common, physiologically unobjectionable direct dyes from the group of cationic, and anionic dyes, disperse dyes, azo dyes, quinone dyes and triphenyl-methane dyes. The direct dyes are contained in the ready-to-use colorant (A) in an amount from about 0.01 to 10 weight percent and preferably from about 0.1 to 5 weight percent.

Each of the compounds of formula (I) and of the compounds of formula (IIa) or (IIb) is contained in the ready-to-use colorant (A) in a total amount from about 0.01 to 10 weight percent and preferably from about 0.1 to 5 weight percent.

As a rule, the compounds of formula (I) and the compounds of formula (IIa) or (IIb) are stored separately from one another and are mixed with the oxidant only just before use. It is also possible, however, provided the compounds of formula (I) and the compounds of formula (IIa) or (IIb) and the oxidant are solids, to package them together and to obtain the ready-to-use colorant (A) just before use by mixing the compounds of formula (I) and the compounds of formula (IIa) or (IIb) and the oxidant with water or with a liquid preparation containing the other components of the colorant. It is also possible, provided the compounds of formula (I) and the compounds of formula (IIa) or (IIb) are solids, to package them together and to prepare the ready-to-use colorant (A) by mixing the compounds of formula (I) and the compounds of formula (IIa) or (IIb) with the oxidant just before use.

The colorant of the invention thus usually consists of several components that are mixed just before use. Preferably, the colorant is provided as a 2-component kit consisting of dye carrier composition (A1) containing the compounds of formula (I) and an additional dye carrier composition (A2) containing the compounds of formula (IIa) or (IIb) and optionally an oxidant, or it is provided as a 3-component kit consisting of a dye carrier composition (A1) containing the compounds of formula (I), another dye carrier composition (A2) containing the compounds of formula (IIa) or (IIb) and a third component (A3) containing an oxidant.

Particularly preferred is a 3-component kit consisting of a dye carrier composition (A1) containing the compounds of formula (I), another dye carrier composition (A2) containing the compounds of formula (IIa) or (IIb) and a third component (A3) containing an oxidant.

Another object of the invention is a multicomponent kit consisting of a preparation of component (A1) and a preparation of component (A2), the oxidant possibly being packaged as component (A3) separately from component (A2), and optionally of an agent for adjusting the pH (an alkalinizing agent or an acid). Naturally, the preparations of components (A1) and (A2) can consist of several individual components that are mixed with one another just before use.

Another possibility is a 2-component kit of which the 1st component consists of a powder containing the compounds of formula (I), the compounds of formula (IIa) or (IIb) and optionally an oxidant, provided the compounds of formula (I) and the compounds of formula (IIa) or (IIb) and the oxidant are solids, and optionally other common powdered cosmetic additives, and the 2nd component of which is water or a liquid cosmetic preparation. Preferred is a 2-component kit of which the 1st component consists of a powder containing the compounds of formula (I), the compounds of formula (IIa) or (IIb) and the oxidant and optionally other common powdered cosmetic additives and the 2nd component of which is water or a liquid cosmetic preparation.

The components (A1) and (A2) and the ready-to-use colorant (A) are provided, for example, in the form of a solution, particularly an aqueous or aqueous-alcoholic solution, a cream, a gel or an emulsion. Their composition consists of a mixture of the compound of formula (I) or compound of formula (IIa) or (IIb) and optionally of an oxidant, with the additives normally used for such preparations.

Commonly used additives to solutions, creams, emulsions, gels or aerosol foams are, for example, solvents such as water, the lower aliphatic alcohols, for example ethanol, n-propanol and isopropanol, or glycols such as glycerol and 1,2-propanediol, furthermore wetting agents or emulsifiers from the classes of anionic, cationic, amphoteric or nonionic surface-active substances, such as the fatty alcohol sulfates, ethoxylated fatty alcohol sulfates, alkyl sulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, perfumes, hair pretreatment agents, conditioners, hair-swelling agents, preservatives, furthermore vaselines, paraffin oil and fatty acids and also hair-care agents such as the cationic resins, lanolin derivatives, cholesterol, pantothenic acid and betaine. The said constituents are used in amounts usually employed for such purposes, for example the wetting agents and emulsifiers at a concentration from about 0.5 to 30 weight percent [in all cases based on component (A1) or (A2)], the thickeners in an amount from about 0.1 to 25 weight percent [in all cases based on component (A1) or (A2)] and the hair-care agents at a concentration from about 0.1 to 5.0 weight percent [in all cases based on component (A1) or (A2)].

The pH of the ready-to-use colorant (A) is in all cases about 6 to 12 and preferably about 7 to 11. The ready-to-use colorant (A) is adjusted to the pH desired for the coloring by addition of an alkalinizing agent, for example ammonia, an amino acid, alkanolamine, alkali metal hydroxide, alkaline earth metal hydroxide, alkali metal acetate, alkaline earth metal acetate, ammonium carbonate, alkali metal carbonate, alkaline earth metal carbonate, alkali metal silicate, alkaline earth metal silicate or ammonium silicate, or by addition of an acid, for example lactic acid, acetic acid, tartaric acid, phosphoric acid, hydrochloric acid, citric acid, ascorbic acid or boric acid.

The ready-to-use colorant is prepared just before use by mixing components (A1) and (A2) or (A1), (A2) and (A3), optionally with addition of an alkalinizing agent or an acid, and is then applied to the fibers, particularly human hair. Depending on the color depth desired, this mixture is allowed to act for about 5 to 60 minutes, preferably about 15 to 30 minutes, at a temperature of about 20 to 50° C. and particularly about 30 to 40° C. The fibers are then rinsed with water, optionally washed with a shampoo and then dried.

The colorant of the invention gives a uniform, intense, brilliant and lasting coloration of the fibers, particularly keratin fibers, for example human hair.

The examples will provide a more detailed explanation of the subject matter without limiting it to these examples.

EXAMPLES

Example 1a

Synthesis of 3,4-dimethyl-2(3H)thiazolone hydrazone hydrochloride

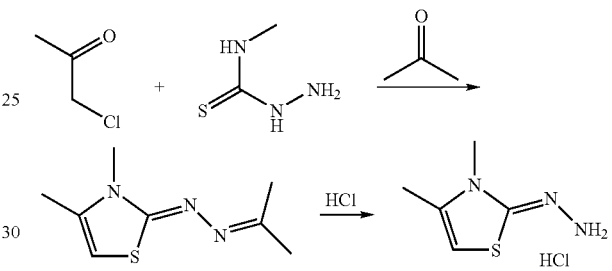

Step A: 3,4-Dimethyl-2(3H)thiazolone-(1-methylethylidene)hydrazone 21 g (200 mmol) of 4-methyl-3-thiosemicarbazide in 1000 mL of acetone was heated at reflux for 2 hours. To this solution was then added dropwise 20.4 g (220 mmol) of chloroacetone. The reaction mixture was allowed to reflux for 7 hours and was then concentrated. The resulting crude product was recrystallized from acetone. This gave 23 g of an orange-colored powder (63% of the theoretical).

Melting point: 139-139.6° C.

$^1$H-NMR (DMSO, 300 MHz): δ=6.72 [s, broad, 1H, H—C(5)]; δ=3.67 (s, 3H, N—CH$_3$); δ=2.27 [d, J=0.9 Hz, 3H, CH$_3$—C(4)]; δ=2.17 (s, 3H, CH$_3$); δ=2.07 (s, 3H, CH$_3$)

$^{13}$C-NMR (DMSO, 300 MHz): δ=169.16; 164.14; 139.02 [C(4)]; 103.36 [C(5)]; 34.47 (CH$_3$N); 24.60; 19.91; 13.53 [CH$_3$(C4)].

MS (ESI): 184 (M$^+$+1)

Step B: 3,4-Dimethyl-2(3H)thiazolone hydrazone hydrochloride 3.5 g (19 mmol) of 3,4-dimethyl-2(3H)thiazolone-(1-methylethylidene) hydrazone from step 1 in 60 mL of 6M hydrochloric acid was heated at 50° C. for 30 minutes. The reaction mixture was then concentrated, and the crude product was recrystallized from ethanol. This gave 2 g (60% of the theoretical) of a pink-colored powder.

Melting point: 156.4-156.6° C.

$^1$H-NMR (DMSO, 300 MHz): δ=6.58 [q, J=0.9 Hz, 1H, H—C(5)]; δ=3.41 (s, 3H, N—CH$_3$); δ=2.18 [d, 0.9 Hz, 3H, CH$_3$—C(4)].

MS (ESI): 144 (M$^+$+1).

$^{13}$C-NMR (DMSO, 300 MHz): δ=172.30 [C(2)]; 138.79 [C(4)]; 101.43 [C(5)]; 32.92 (CH$_3$N); 13.40 [CH$_3$(C4)];
CHN analysis: [C$_5$H$_9$N$_3$S (0.96 HCl)(0.5 EtOH)]:

|  | % C | % H | % N | % S | % Cl |
|---|---|---|---|---|---|
| Calculated: | 35.81 | 6.49 | 20.88 | 15.93 | 16.90 |
| Found: | 35.20 | 6.30 | 21.00 | 15.40 | 16.80 |

Example 1b

Synthesis of 3,4,5-trimethyl-2(3H)thiazolone hydrazone hydrochloride 3,4,5-Trimethyl-2(3H)thiazolone hydrazone hydrochloride was prepared from 4-methyl-3-thiosemicarbazide and 3-chloro-2-butanone by a method similar to that used in Example (1a).
$^1$H-NMR (DMSO/D$_2$O, 300 MHz): δ=3.55 (s, 3H, N—CH$_3$); δ=2.16 (s, 3H, CH$_3$); δ=2.12 (s, 3H, CH$_3$).
ESI-MS: 157 [M$^+$] (100)

Examples 2-4

Colorants with 3-methyl-2(3H)benzothiazolone hydrazone hydrochloride

Component (A1)
    4.00 g of decylpolyglucose, 50% aqueous solution
    0.20 g of disodium ethylenediaminetetraacetate hydrate
    5.00 g of ethanol
    0.58 g of 3-methyl-2(3H)benzothiazolone hydrazone hydrochloride hydrate to 100.00 g water, demineralized Component (A2)
    Y g of aromatic enamine of formula ((IIa) or (IIb) as per Table 1
    0.40 g of potassium persulfate The foregoing constituents were mixed uniformly with one another at room temperature (20-25° C.) or with slight heating (35-40° C.). The pH of the ready-to-use colorant (A) was adjusted to the value given in Table 1 with sodium hydroxide solution, sodium carbonate or ammonia.

The ready-to-use colorant was applied to bleached hair and uniformly distributed with a brush. After an exposure time of 30 min at 40° C., the hair was rinsed with lukewarm water, washed with a commercial shampoo, rinsed with lukewarm water and then dried.

The amount of the aromatic enamine of formula (IIA) or (IIb) used and the colorations obtained are summarized in the following Table 1.

TABLE 1

| Example No. | Enamine Used (amount in g) | pH | Color |
|---|---|---|---|
| 2 | 1,2,3,4-tetramethyl-3H-indolium-chloride (0.52 g) | 8.6 | ruby red |
| 3 | 3-ethyl-1,2,3-trimethyl-3H-indolium chloride (0.56 g) | 9.2 | ruby red |
| 4 | 1-ethyl-2,3,3-trimethyl-5-methoxy-3H-indolium tetrafluoroborate (0.76 g) | 8.8 | strawberry red |

Examples 5-8

Colorants with 3,4-dimethyl-2(3H)thiazolone hydrazone hydrochloride

Component (A1)
    4.00 g of decylpolyglucose, 50% aqueous solution
    0.20 g of disodium ethylenediaminetetraacetate hydrate
    5.00 g of ethanol
    0.45 g of 3,4-dimethyl-2(3H)thiazolone hydrazone hydrochloride
    to 100.00 g water, demineralized Component (A2)
    Y g of aromatic enamine of formula (IIa) or (IIb) as per Table 2
    0.40 g of potassium persulfate The foregoing constituents were mixed uniformly with one another at room temperature (20-25° C.) or with slight heating (35-40° C.). The pH of the ready-to-use colorant (A) was adjusted to the value given in Table 2 with sodium hydroxide solution, sodium carbonate or ammonia.

The ready-to-use colorant was applied to bleached hair and uniformly distributed with a brush. After an exposure time of 30 min at 40° C., the hair was rinsed with lukewarm water, washed with a commercial shampoo, rinsed with lukewarm water and then dried.

The amount of the aromatic enamine of formula (IIA) or (IIb) used and the colorations obtained are summarized in the following Table 2.

TABLE 2

| Example No. | Enamine Used (amount in g) | pH | Color |
|---|---|---|---|
| 5 | 1,2,3,3-tetramethyl-3H-indolium hydrogen sulfate (0.68 g) | 9.2 | strawberry red |
| 6 | 3-ethyl-1,2,3-trimethyl-3H-indolium chloride (0.56 g) | 9.2 | strawberry red |
| 7 | 1-ethyl-2,3,3-trimethyl-5-methoxy-3H-indolium tetrafluoroborate (0.76 g) | 8.8 | violet |
| 8 | 3-ethyl-2-methylbenzothiazolium ptoluenesulfonate (0.87 g) | 8.8 | orange |

Examples 9-11

Colorants with 3,4,5-trimethyl-2(3H)thiazolone hydrazone hydrochloride

Component (A1)
    4.00 g of decylpolyglucose, 50% aqueous solution
    0.20 g of disodium ethylenediaminetetraacetate hydrate
    5.00 g of ethanol
    0.48 g of 3,4,5-trimethyl-2(3H)thiazolone hydrazone hydrochloride
    to 100.00 g water, demineralized Component (A2)
    Y g of aromatic enamine of formula (IIa) or (IIb) as per Table 3
    0.40 g of potassium persulfate The foregoing constituents were mixed uniformly with one another at room temperature (20-25° C.) or with slight heating (35-40° C.). The pH pf the ready-to-use colorant (A) was adjusted to the value given in Table 3 with sodium hydroxide solution, sodium carbonate or ammonia.

The ready-to-use colorant was applied to bleached buffalo hair and uniformly distributed with a brush. After an exposure time of 30 min at 40° C., the hair was rinsed with lukewarm water, washed with a commercial shampoo, rinsed with lukewarm water and then dried.

The amount of the aromatic enamine of formula (IIA) or (IIb) used and the colorations obtained are summarized in the following Table 3.

TABLE 3

| Example No. | Enamine used (amount in g) | pH | Color |
|---|---|---|---|
| 9 | 1,2,3,3-tetramethyl-3H-indolium hydrogen sulfate (0.68 g) | 9.2 | pink |
| 10 | 3-ethyl-1,2,3-trimethyl-3H-indolium chloride (0.56 g) | 9.2 | pink |
| 11 | 1-ethyl-2,3,3-trimethyl-5-methoxy-3H-indolium tetrafluoroborate (0.76 g) | 8.8 | violet |

Examples 12-14

Colorants with 3,4-dimethyl-2(3H)thiazolone hydrazone hydrochloride

Component (A1)

4.00 g of decylpolyglucose, 50% aqueous solution
0.20 g of disodium ethylenediaminetetraacetate hydrate
5.00 g of ethanol
to 100.00 g water, demineralized Component (A2)

0.45 g of 3,4-dimethyl-2(3H)thiazolone hydrazone hydrochloride
Y g of aromatic enamine of formula (IIa) or (IIb) as per Table 4.

Component (A2) was dissolved in 84 g of Component (A1) at room temperature (20-25° C.) or with slight heating (35-40° C.) and the solution was uniformly mixed with 16 g of a 6% aqueous hydrogen peroxide solution. The pH of the ready-to-use colorant (A) was adjusted to the value given in Table 4 with sodium hydroxide solution, sodium carbonate or ammonia.

The ready-to-use colorant was applied to bleached hair and uniformly distributed with a brush. After an exposure time of 30 min at 40° C., the hair was rinsed with lukewarm water, washed with a commercial shampoo, rinsed with lukewarm water and then dried.

The amount of the aromatic enamine of formula (IIA) or (IIb) used and the colorations obtained are summarized in the following Table 4.

TABLE 4

| Example No. | Enamine Used (amount in g) | pH | Color |
|---|---|---|---|
| 12 | 1,2,3,3-tetramethyl-3H-indolium hydrogen sulfate (0.68 g) | 9.6 | pink |
| 13 | 3-ethyl-1,2,3-trimethyl-3H-indolium chloride (0.56 g) | 9.1 | strawberry red |
| 14 | 1-ethyl-2,3,3-trimethyl-5-methoxy-3H-indolium tetrafluoroborate (0.76 g) | 9.2 | violet |

Unless otherwise indicated, all percentages given in the present patent application are by weight.

The invention claimed is:

1. A ready-to-use agent for coloring keratin fibers, wherein said ready-to-use agent contains:
    (a) at least one hydrazone derivative of formula (I), or a physiologically compatible salt thereof:

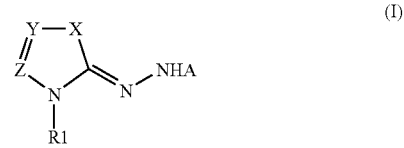

(I)

wherein X denotes oxygen, sulfur or N—R2,
Y denotes C—R3 or nitrogen, and
Z denotes C—R4 or nitrogen,
provided that a heterocyclic ring in said at least one hydrazone derivative contains at the most three hetero atoms;
A denotes hydrogen, an acetyl group, a trifluoroacetyl group, a formyl group, a ($C_1$-$C_6$)-alkyl-sulfonyl group, or an arylsulfonyl group;
R1 and R2 are the same or different and, independently of each other, denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a —C(O)—($C_1$-$C_{12}$)-alkyl group, a —C(O)-phenyl group, a —C(O)NH—($C_1$-$C_{12}$)-alkyl group, a —C(O)NH-phenyl group, a phenyl group, or a benzyl group;
R3 and R4 can be the same or different and, independently of each other, denote hydrogen, a halogen atom, a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a di($C_1$-$C_{12}$)-alkylamino group, a carboxyl group, a —C(O)O—($C_1$-$C_{12}$)-alkyl group, a —C(O)O-phenyl group, a phenyl group, or a naphthyl group; and when Y and Z denote C—R3 and C—R4, R3 and R4 together with a remainder of the hydrazone derivative can form a heterocyclic, carbocyclic, saturated or unsaturated ring system;
    (b) at least one aromatic enamine of formula (IIa), or an acid addition salt thereof of formula (IIb):

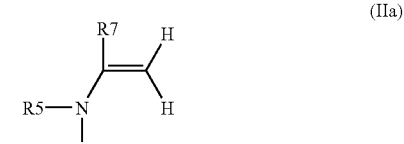

(IIa)

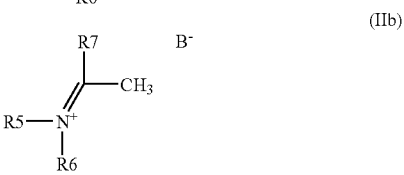

(IIb)

wherein
R5 denotes a mononuclear or polynuclear aromatic group,
R6 denotes a ($C_1$-$C_{12}$)-alkyl group, a monohydroxy-($C_1$-$C_{12}$)-alkyl group, or a mono-($C_1$-$C_6$)-alkoxy-($C_1$-$C_6$)-alkyl group, wherein oxygen atoms can be present between carbon atoms of the alkyl group, and R7 denotes a ($C_1$-$C_{12}$)-alkyl group, a mono-($C_1$-$C_6$)-alkoxy-($C_1$-$C_6$)-alkyl group, a ($C_1$-$C_6$)-alkylene-($C_1$-$C_6$) group, a ($C_1$-$C_6$)-alkoxy-($C_1$-$C_6$)-alkylene group, —O—, NR8- or —S—;

wherein R8 denotes a ($C_1$-$C_{12}$)-alkyl group, a mono-($C_1$-$C_6$)-alkoxy-($C_1$-$C_6$)-alkyl group, a monohydroxy-($C_1$-$C_{12}$)-alkyl group, or hydrogen, and wherein R5 and R7 together with a nitrogen atom and a carbon atom of the aromatic enamine or the acid addition salt thereof form a cyclic linkage, and B⁻ denotes an anion of an organic or inorganic acid; and (c) at least one oxidant.

2. The agent as defined in claim 1, wherein X denotes sulfur, Y denotes C—R3, Z denotes C—R4 and A denotes hydrogen.

3. The agent as defined in claim 1, wherein said at least one hydrazone derivative of the formula (I) is selected from the group consisting of 3-methyl-2(3H)-thiazolone hydrazone; 3,4-dimethyl-2(3H)-thiazolone hydrazone; 4-tert.butyl-3-methyl-2(3H)-thiazolone hydrazone; 3-methyl-4-phenyl-2(3H)-thiazolone hydrazone; 3-methyl-4-(4-tolyl)-2(3H)-thiazolone hydrazone; 4-(4-methoxy)phenyl-3-methyl-2(3H)-thiazolone hydrazone; 4-(4-ethoxy)phenyl-3-methyl-2(3H)-thiazolone hydrazone; 4-(4-bromophenyl)-3-methyl-2(3H)-thiazolone hydrazone; 4-(3-bromophenyl)-3-methyl-2(3H)-thiazolone hydrazone; 4-(4-chlorophenyl)-3-methyl-2(3H)-thiazolone hydrazone; 4-(3-chlorophenyl)-3-methyl-2(3H)-thiazolone hydrazone; 3-methyl-4-(4-nitrophenyl)-2(3H)-thiazolone hydrazone; 3-methyl-4-(3-nitrophenyl)-2(3H)thiazolone hydrazone; 4-[(1,1'-biphenyl)-4-yl]-3-methyl-2(3H)-thiazolone hydrazone; ethyl 2-hydrazono-2,3-dihydro-3-methyl-4-thiazole-carboxylate; 3,4,5-trimethyl-2(3H)-thiazolone hydrazone; 3,4-dimethyl-5-phenyl-2(3H)-thiazolone hydrazone; 3,5-dimethyl-4-phenyl-2(3H)-thiazolone hydrazone; 4,5-diphenyl-3-methyl-2(3H)-thiazolone hydrazone; 5-ethyl-3-methyl-4-phenyl-2(3H)-thiazolone hydrazone; 4-(4-bromo-phenyl)-3-methyl-5-phenyl-2(3H)-thiazolone hydrazone; 3-methyl-5-phenyl-4-(4-tolyl)-2(3H)-thiazolone hydrazone; 5-(4-chlorophenyl)-4-phenyl-3-methyl-2(3H)-thiazolone hydrazone; 5-(4-chlorophenyl)-4-(4-methoxyphenyl)-3-methyl-2(3H)-thiazolone hydrazone; ethyl 2-hydrazono-2,3-dihydro-3,4-dimethyl-4-thiazole carboxylate; 4-amino-2-hydrazono-2,3-dihydro-3-methyl-5-thiazole carbonitrile; 4,5-dimethyl-3-ethyl-2(3H)-thiazolone hydrazone; ethyl 2-hydrazono-2,3-dihydro-3-ethyl-4-methyl-thiazolecarboxylate; 5-methyl-3-(1-methylethyl)-4-phenyl-2(3H)-thiazolone hydrazone; 4,5-diphenyl-3-(1-methylethyl)-2(3H)-thiazolone hydrazone; 4,5-diphenyl-3-propyl-2(3H)-thiazolone hydrazone; 3-butyl-4,5-diphenyl-2(3H)-thiazolone hydrazone; 4,5-diphenyl-3-(2-methyl-propyl)-2(3H)-thiazolone hydrazone; 3-(2-propenyl)-2(3H)-thiazolone hydrazone; 4-methyl-3-(2-propenyl)-2(3H)-thiazolone hydrazone; 4-tert.-butyl-3-(2-propenyl)-2(3H)-thiazolone hydrazone; 4-phenyl-3-(2-propenyl)-2(3H)-thiazolone hydrazone; 4,5-diphenyl-3-(2-propenyl)-2(3H)-thiazolone hydrazone; 3-hydroxyethyl-2(3H)-thiazolone hydrazone; 3-hydroxyethyl-4-methyl-2(3H)-thiazolone hydrazone; 3-aminoethyl-2(3H)-thiazolone hydrazone; 3-aminoethyl-4-methyl-2(3H)-thiazolone hydrazone; 3-phenyl-2(3H)-thiazolone hydrazone; 4-methyl-3-phenyl-2(3H)-thiazolone hydrazone; 3,4-diphenyl-2(3H)-thiazolone hydrazone; 4-p-biphenylyl-3-phenyl-2(3H)-thiazolone hydrazone; 4-(4-methoxy)-phenyl-3-phenyl-2(3H)-thiazolone hydrazone; 4-tert.butyl-3-phenyl-2(3H)-thiazolone hydrazone; 3,4-diphenyl-5-methyl-2(3H)-thiazolone hydrazone; 3,4,5-triphenyl-2(3H)-thiazolone hydrazone; 4,5-dimethyl-3-(phenylmethyl)-2(3H)-thiazolone hydrazone; ethyl 2-hydrazono-2,3-dihydro-3-[(phenylamino)carbonyl]-4-methylthiazolecarboxylate; 3-methyl-4,5,6,7-tetrahydro-2(3H)-benzothiazolone hydrazone; 3-methyl-2(3H)benzothiazolone hydrazone; 3,6-dimethyl-2(3H)benzothiazolone hydrazone; 6-chloro-3-methyl-2(3H)benzothiazolone hydrazone; 7-chloro-3-methyl-2(3H)benzothiazolone hydrazone; 6-hydroxy-3-methyl-2(3H)benzothiazolone hydrazone; 5-methoxy-3-methyl-2(3H)benzothiazolone hydrazone; 7-methoxy-3-methyl-2(3H)benzothiazolone hydrazone; 5,6-dimethoxy-3-methyl-2(3H)benzothiazolone hydrazone; 5-ethoxy-3-methyl-2(3H)benzothiazolone hydrazone; 6-ethoxy-3-methyl-2(3H)benzothiazolone hydrazone; 3-methyl-5-nitro-2(3H)benzothiazolone hydrazone; 3-methyl-6-nitro-2(3H)benzothiazolone hydrazone; 5-acetamido-3-methyl-2(3H)benzo-thiazolone hydrazone; 6-acetamido-3-methyl-2(3H)benzothiazolone hydrazone; 5-anilino-3-methyl-2(3H)benzothiazolone hydrazone; 6-anilino-3-methyl-2(3H)benzothiazolone hydrazone; 2-hydrazono-2,3-dihydro-3-methyl-6-benzothiazole carboxylic acid; 2-hydrazono-2,3-dihydro-3-methyl-4-benzothiazole sulfonic acid, 2-hydrazono-2,3-dihydro-3-methyl-5-benzothiazole sulfonic acid; 2-hydrazono-2,3-dihydro-3-methyl-6-benzothiazole sulfonic acid; 2-hydrazono-2,3-dihydro-3-methyl-7-benzothiazole sulfonic acid; 2-hydrazono-2,3-dihydro-N,N,3-trimethyl-6-benzothiazole sulfonamide; [(2-hydrazo-no-2,3-dihydro-3-methyl-6-benzothiazolyl)oxy]-acetic acid hydrazide; 3-methylnaphtho-[2,3-d]-thiazol-2(3H)one hydrazone; 3-ethyl-2(3H)benzothiazolone hydrazone; 6-ethoxy-3-ethyl-2(3H)benzothiazolone hydrazone; 3-propyl-2(3H)benzothiazolone hydrazone; 3-butyl-2(3H)benzothiazolone hydrazone; 3-hexyl-2(3H)benzothiazolone hydrazone; 3-hydroxyethyl-2(3H)benzothiazolone hydrazone; 3-aminoethyl-2(3H)benzothiazolone hydrazone; 3-p-methylbenzyl-2(3H)benzothiazolone hydrazone; 2-hydrazono-2,3-dihydro-3-(2-hydroxyethyl)-6-benzothiazole carboxylic acid; 2-hydrazono-2,3-dihydro-6-methoxy-3(2H)benzothiazole propanesulfonic acid; 6-hexadecyloxy-2-hydrazono-3(2H)benzothiazole propanesulfonic acid; ethyl 2-keto-3-benzothiazoline acetate hydrazone; 3-acetyl-2(3H)-benzothiazolone hydrazone; and 2-hydrazono-3(2H)benzothiazole carboxaldehyde.

4. The agent as defined in claim 1, where in the formula (IIa)/(IIb) R5 and R7 together with the nitrogen atom and the carbon atom of the aromatic enamine or the acid addition salt thereof form the cyclic linkage.

5. The agent as defined in claim 4, wherein R7 is linked to the aromatic R5 group with a carbon atom thereof standing in an ortho-position in relation to the carbon atom of the aromatic enamine or the acid addition salt thereof.

6. The agent as defined in claim 1, wherein the at least one acid addition salt of the formula (IIb) is selected from the group consisting of 1,2,3,3-tetramethyl-3H-indolium chloride, 1,2,3,3-tetramethyl-3H-indolium bromide; 1,2,3,3-tetramethyl-3H-indolium hydrogen sulfate; 1,2,3,3-tetramethyl-3H-indolium sulfate; 1,2,3,3-tetramethyl-3H-indolium tetrafluoroborate; 3-ethyl-1,2,3-trimethyl-3H-indolium chloride; 3-ethyl-1,2,3-trimethyl-3H-indolium bromide; 3-ethyl-1,2,3-trimethyl-3H-indolium sulfate; 3-ethyl-1,2,3-trimethyl-3H-indolium tetrafluoroborate; 1-ethyl-5-methoxy-2,3,3-trimethyl-3H-indolium chloride; 1-ethyl-5-methoxy-2,3,3-trimethyl-3H-indolium bromide; 1-ethyl-5-methoxy-2,3,3-trimethyl-3H-indolium sulfate; 1-ethyl-5-methoxy-2,3,3-trimethyl-3H-indolium tetrafluoroborate; 5-methoxy-1,2,3,3-tetramethyl-3H-indolium chloride; 5-methoxy-1,2,3,3-tetramethyl-3H-indolium bromide;

5-methoxy-1,2,3,3-tetramethyl-3H-indolium sulfate; 5-methoxy-1,2,3,3-tetramethyl-3H-indolium tetrafluoroborate; 5-nitro-1,2,3,3-tetramethyl-3H-indolium chloride; 5-nitro-1,2,3,3-tetramethyl-3H-indolium bromide, 5-nitro-1,2,3,3-tetramethyl-3H-indolium sulfate; 5-nitro-1,2,3,3-tetramethyl-3H-indolium tetrafluoroborate; 2,3-dimethylbenzothiazolium chloride; 2,3-dimethylbenzothiazolium bromide; 2,3-dimethylbenzothiazolium iodide; 2,3-dimethylbenzothiazolium methylsulfate; 3-ethyl-2-methylbenzothiazolium chloride; 3-ethyl-2-methylbenzothiazolium bromide; 3-ethyl-2-methylbenzothiazolium iodide; 3-ethyl-2-methylbenzothiazolium methylsulfate; and 3-ethyl-2-methylbenzothiazolium p-toluene sulfonate.

7. The agent as defined in claim 1, wherein said at least one oxidant is selected from the group consisting of hydrogen peroxide, addition compounds of hydrogen peroxide, persalts, peracids, and enzymatic oxidation systems.

8. The agent as defined in claim 1, wherein said at least one oxidant is selected from the group consisting of hydrogen peroxide, addition products of hydrogen peroxide, and persalts.

9. The agent as defined in claim 1, containing each of the at least one hydrazone derivative of formula (I), the at least one aromatic enamine of the formula (IIa) or acid addition salt thereof of formula (IIb), and the at least one oxidant in a total amount from 0.01 to 10 weight percent.

10. The agent as defined in claim 1, further comprising from 0.01 to 10 weight percent of a physiologically harmless direct dye and wherein said direct dye is selected from the group consisting of cationic dyes, anionic dyes, disperse dyes, nitro dyes, azo dyes, quinone dyes, and triphenylmethane dyes.

11. The agent as defined in claim 1, having a pH from 7 to 11.

12. The agent as defined in claim 1, consisting of a hair colorant.

13. A two-component kit consisting of one dye carrier composition (A1) and another dye carrier composition (A2), which is separate from the one dye carrier composition (A1);
wherein said one dye carrier composition (A1) contains the at least one hydrazone derivative of the formula (I) as defined in claim 1 and said another dye carrier composition (A2) contains an oxidant and the at least one aromatic enamine of the formula (IIa) or acid addition salt thereof of the formula (IIb) as defined in claim 1.

14. A three-component kit consisting of one dye carrier composition (A1), another dye carrier composition (A2), and a third component separate from each other;
wherein said one dye carrier composition (A1) contains the at least one hydrazone derivative of the formula (I) as defined in claim 1, said another dye carrier composition (A2) contains an oxidant and the at least one aromatic enamine of the formula (IIa) or acid addition salt thereof of the formula (IIb) as defined in claim 1, and said third component contains an agent for adjusting pH.

15. A two-component kit consisting of a powdered dye carrier composition (A1) and a liquid cosmetic preparation (A2) separate from each other, and
wherein said powdered dye carrier composition (A1) contains an oxidant, the at least one hydrazone derivative of the formula (I) as defined in claim 1, and the at least one aromatic enamine of the formula (IIa) or acid addition salt thereof of the formula (IIb) as defined in claim 1, as well as optionally other powdered cosmetic additive ingredients.

16. A three-component kit consisting of one dye carrier composition (A1), another dye carrier composition (A2), and a third component separate from each other;
wherein said one dye carrier composition (A1) contains the at least one hydrazone derivative of the formula (I) as defined in claim 1, said another dye carrier composition (A2) contains the at least one aromatic enamine of the formula (IIa) or acid addition salt thereof of the formula (IIb) as defined in claim 1, and said third component contains an oxidant.

17. A method for coloring hair, said method comprising the steps of:
a) applying a colorant to the hair;
b) allowing the colorant applied in step a) to act on the hair for an acting time of from 5 to 60 minutes at a temperature from 20 to 50° C.; and
c) after the acting time has elapsed, rinsing the hair with water, optionally washing the hair with a shampoo and then drying the hair;
wherein said colorant is the ready-to-use agent for coloring as defined in claim 1.

* * * * *